United States Patent [19]
Eddleman et al.

[11] Patent Number: 5,783,075
[45] Date of Patent: Jul. 21, 1998

[54] DISPOSABLE DIALYZER APPARATUS

[75] Inventors: Roy Eddleman, Los Angeles; F. Jesus Martinez, Mission Viejo; William Martin, Lake Forest; Dieter Stute, San Juan Capistrano, all of Calif.

[73] Assignee: Spectrum Medical Laboratories, Inc., Laguna Hills, Calif.

[21] Appl. No.: 880,970

[22] Filed: Jun. 23, 1997

[51] Int. Cl.⁶ .................. B01D 61/28; B01D 61/30
[52] U.S. Cl. .............. 210/232; 210/242.1; 210/644
[58] Field of Search .................. 210/644, 232, 210/242.1, 85, 321.6; 422/101, 102, 104

[56] References Cited

U.S. PATENT DOCUMENTS

| | | |
|---|---|---|
| 4,699,706 | 10/1987 | Burd et al. |
| 4,828,706 | 5/1989 | Eddleman ............... 210/644 |
| 5,324,428 | 6/1994 | Flaherty ............... 210/644 |
| 5,503,741 | 4/1996 | Clark ................... 210/644 |

*Primary Examiner*—John Kim
*Attorney, Agent, or Firm*—Edgar W. Averill, Jr.

[57] ABSTRACT

A disposable dialysis apparatus which floats in a dialysate solution. The apparatus has a membrane support ring with a central opening surrounded by a downwardly extending tube. The open bottom of the tube supports a dialysis membrane. After the membrane has been loaded with a sample, the membrane is closed and the apparatus is suspended in the dialysate solution.

17 Claims, 6 Drawing Sheets

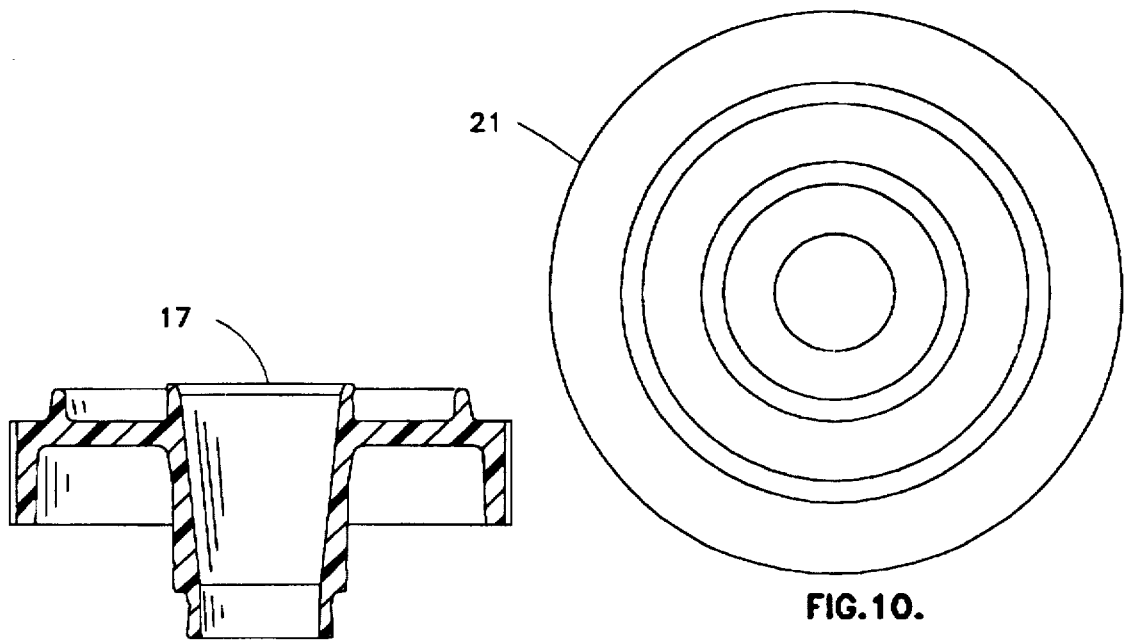
FIG.7.
FIG.10.
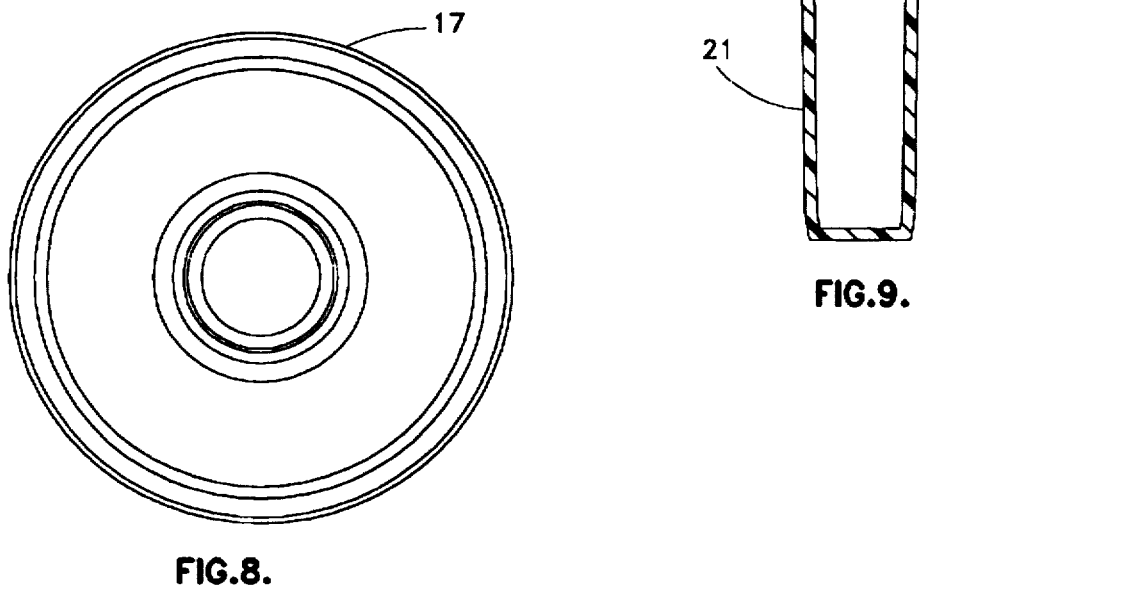
FIG.8.
FIG.9.

DISPOSABLE DIALYZER APPARATUS

BACKGROUND OF THE INVENTION

The field of the invention is dialysis devices and the invention is related more particularly to dialysis devices for small samples.

Various devices are used for performing dialysis operations on samples. One device which is designed to float in a dialysate is shown in U.S. Pat. No. 5,324,428 assigned to the assignee of the present invention. A commonly used dialysis is shown in U.S. Pat. No. 4,828,706. In this device a weighted clamp and an unweighted clamp are affixed to a length of dialysis membrane in the shape of a tube. The clamped length is suspended in a dialysate solution. Another floating membrane is described in U.S. Pat. No. 5,503,741. In this device, two membrane sheets are captured in a polymeric holder. The holder is provided with an opening through which a sample can be injected. The device is then supported in a float so that it may be suspended in the dialysate.

It is important for research purposes to have a variety of dialysis devices to accommodate different sample sizes and molecular weight cutoffs. It is also important that the device be easy to load and unload. The prior art devices have had experiences in those areas.

BRIEF SUMMARY OF THE INVENTION

It is an object of the present invention to provide a series of dialysis units which may be readily made to process various sample sizes and also may be made with easily selected molecular weight cutoff ranges. The present invention is for a disposable dialysis apparatus having a membrane support ring having a membrane support tube in its center. The support tube has an open top and an open bottom. An insert member having an insert cup may be placed so that its insert cup fits within the membrane support tube. The insert cup has a closed bottom which extends below the open bottom of the membrane support tube. A cup shaped membrane is affixed about the open bottom of the membrane support tube. The cup shaped membrane is formed so that it has a closed bottom. Preferably, the insert member extends beyond the membrane support ring to facilitate the lifting of the apparatus from the dialysate solution. Also preferably, the unit is provided with means to capture air so that it floats with the upper portion significantly above the dialysate solution.

BRIEF DESCRIPTION OF THE DRAWINGS

FIG. 7 is a cross-sectional side view of the membrane support ring of the dialysis apparatus of FIG. 1.

FIG. 8 is a top view of the membrane support ring of FIG. 7.

FIG. 9 is a cross-sectional side view of the insert member of the dialysis apparatus of FIG. 1.

FIG. 10 is a top view of the insert member of FIG. 9.

DESCRIPTION OF THE PREFERRED EMBODIMENTS

Figure 1:
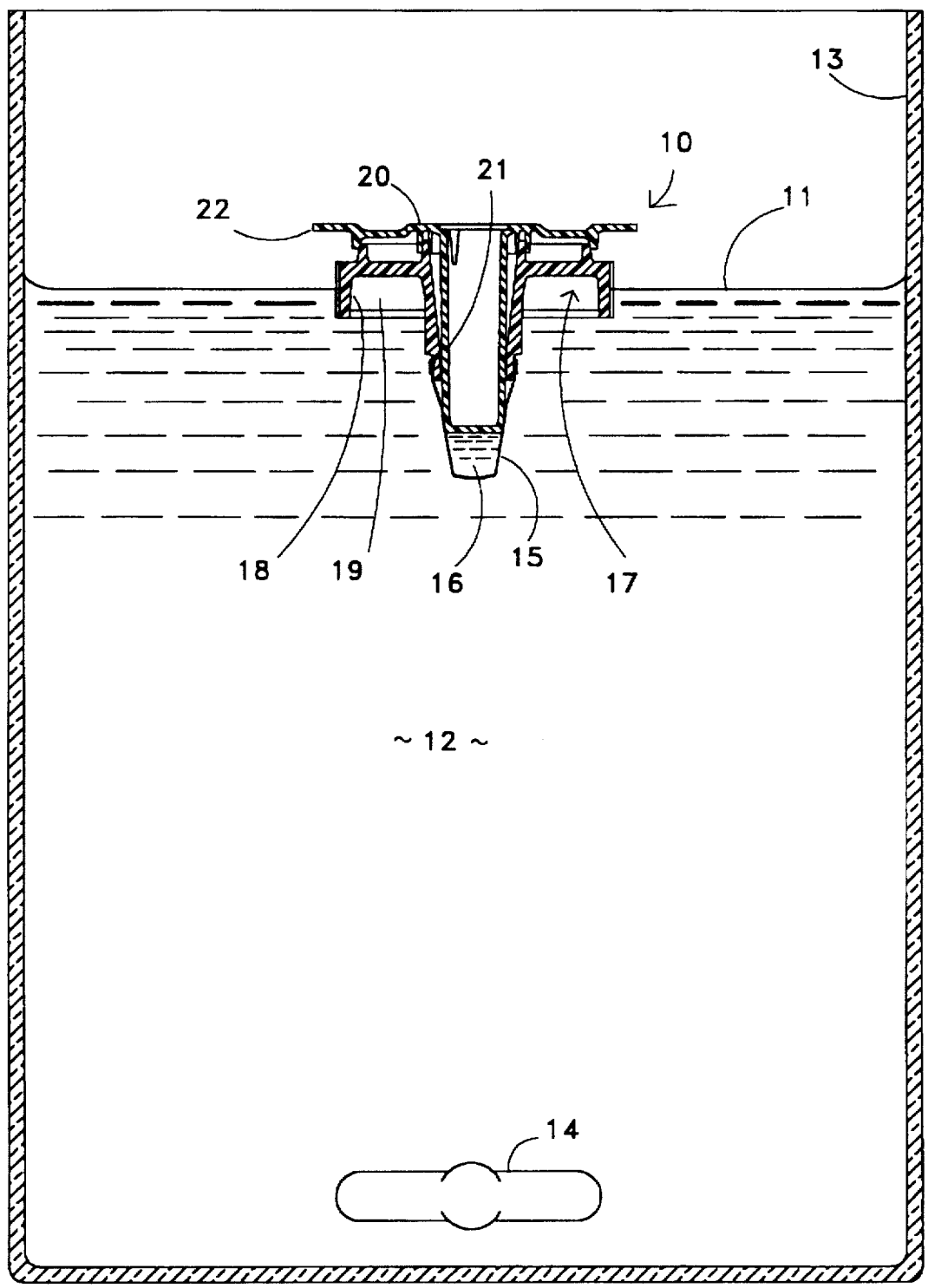
FIG. 1 is a diagrammatic side view showing the dialysis apparatus of the present invention floating on the surface of a dialysate solution.

The dialysis apparatus of the present invention is shown in cross-sectional side view in FIG. 1 and indicated generally by reference character 10. Dialysis apparatus 10 is suspended on the upper surface 11 of dialysate solution 12. Dialysate solution 12 is contained in a beaker 13 provided with a magnetic stirrer 14.

The dialysis apparatus 10 has a membrane cup 15 which contains a sample 16 to be dialyzed. Membrane cup 15 is held to membrane support ring 17. Membrane support ring 17 has an outer ring 18 which creates an air capture space 19 which helps to cause the apparatus 10 to float significantly above upper surface 11 so that it may be removed without the user's fingers contacting the dialysate solution 12. An insert member 20 has an insert cup 21 and an outer ring 22 which provides an easy grip for placing and removing the dialysis apparatus 10 from the dialysis solution 12.

Figures 2, 3:
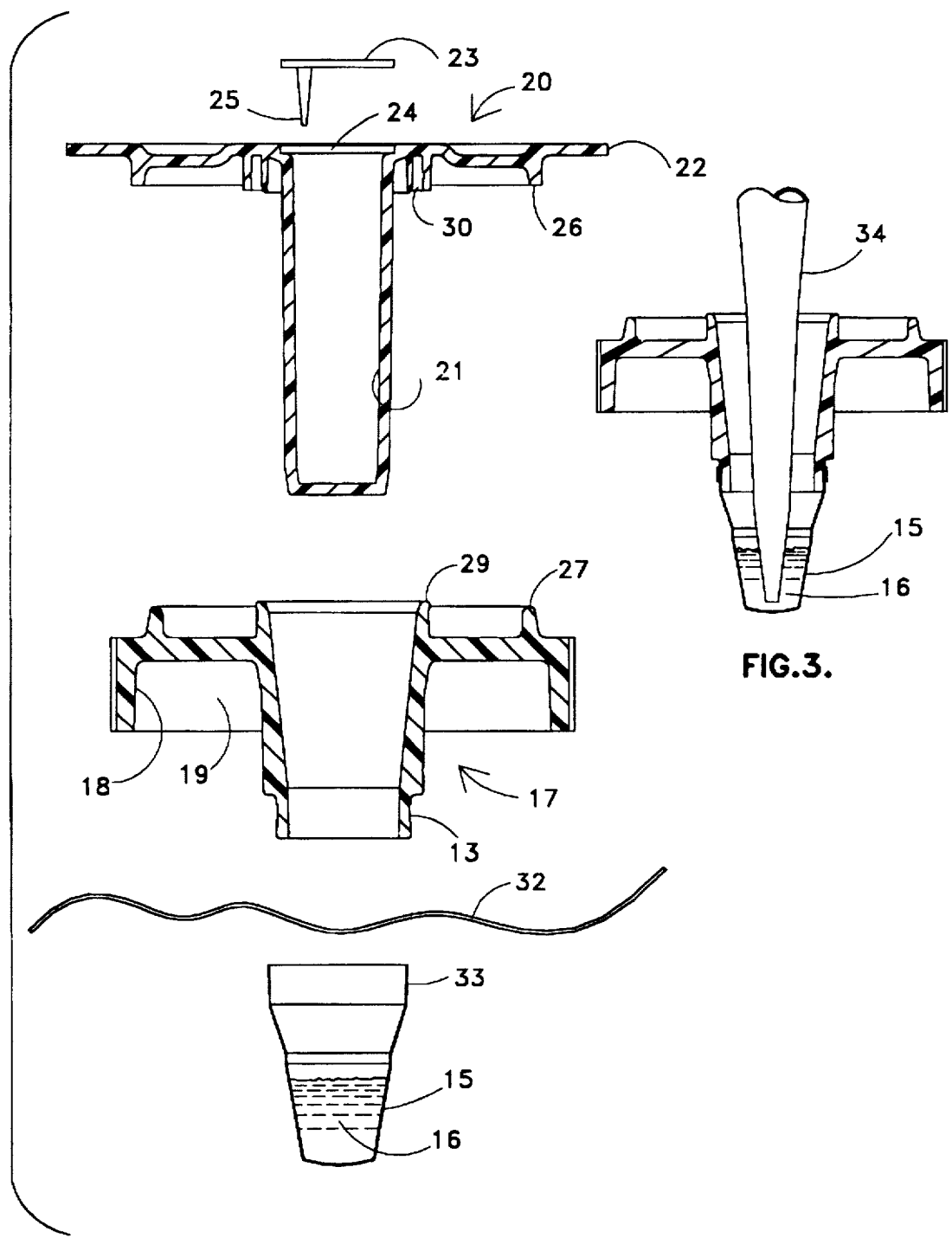
FIG. 2 is an exploded side view partly in cross section of the dialysis apparatus of FIG. 1.
FIG. 3 is a side view of a portion of the dialysis apparatus of FIG. 1 showing the insertion of a sample insertion tube.
Figure 4:
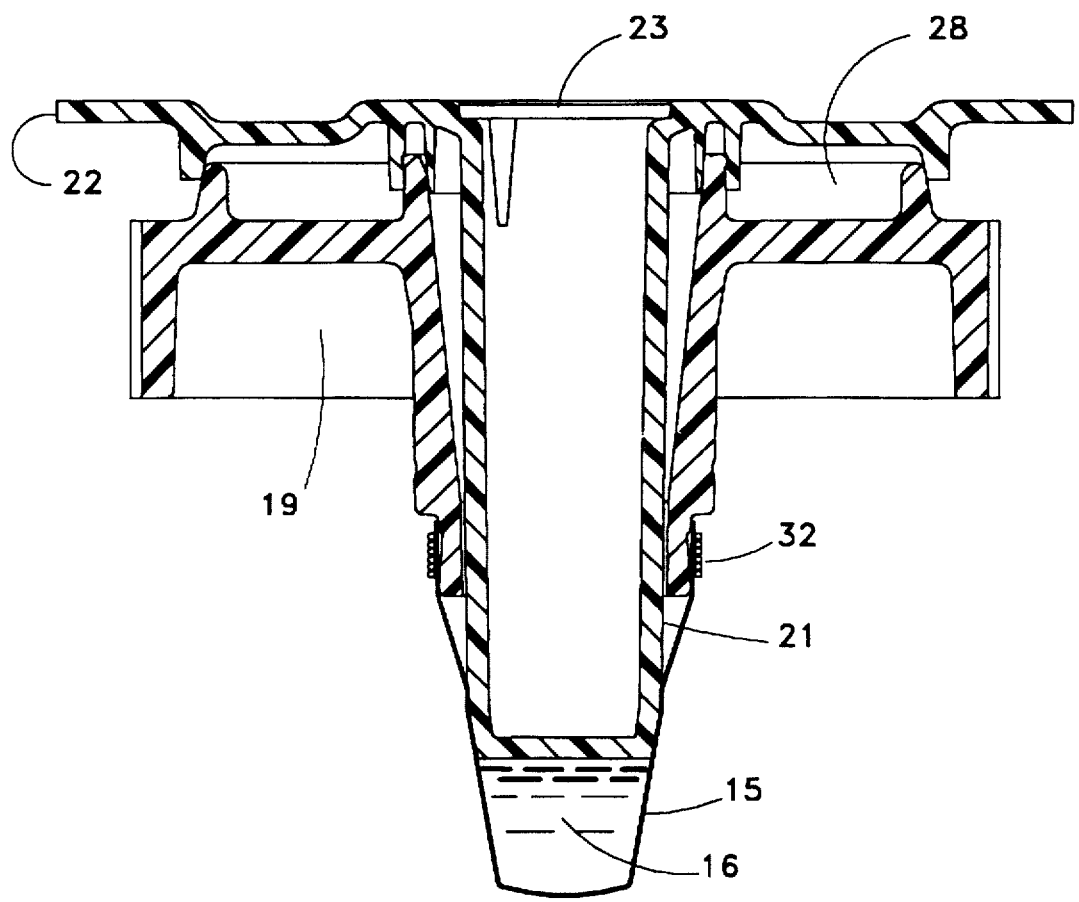
FIG. 4 is a side cross-sectional view of the dialysis apparatus of FIG. 1.

Further details of the dialysis apparatus 10 are shown in FIG. 2. The membrane cup 15 may be formed with different molecular weight cutoffs and is preferably formed by dipping and are made from regenerated cellulose and cellulose esters. The dialysis apparatus may be sterilized by gamma radiation. They may be provided with a wide range of molecular weight cutoffs, typically including 3,500, 8,000, 15,000, 25,000 and 60,000 Daltons to retain biomolecules of this size. It is appropriate to provide a color coded cap 23 which can be matched to the combination of sample size and molecular weight cutoff of the particular apparatus assembled. Color coded cap 23 fits snugly into a recess 24 and includes a guide pin 25 to assist in assembly. Insert member 20 preferably cooperates with membrane support ring 17 to provide a closed air chamber in the event the air capture space 19 inadvertently becomes filled with dialysate solution. Upper flange ring 26 mates with lower flange ring 27 to seal the outer edge of captured air space 28 shown in FIG. 4. The inner edge of air space 28 is formed by the insertion of inner ring 29 in circular groove 30.

The membrane cup 15 is secured to a tie cone 31 at the base of membrane support ring 30 by tying it with a suture 32 around the suture tie ring 33 of membrane cup 15. Of course, other holding methods may be used in place of suture 32 such as an 0ring, heat shrink ring or crimped ring.

The sutured membrane is shown in FIG. 3 where a pipette tip 34 is shown inserted into the membrane cup 15 to insert the sample 16. After the sample 16 has been placed into membrane cup 15, insert member 20 is placed therein to provide the assembled unit shown in FIG. 4. The insert cup 21 is sized dependent upon the sample size of the apparatus. For larger sizes, insert cup 21 would be shorter and conversely, for smaller sample sizes, insert cup 21 would extend further into membrane cup 15.

Figure 5:
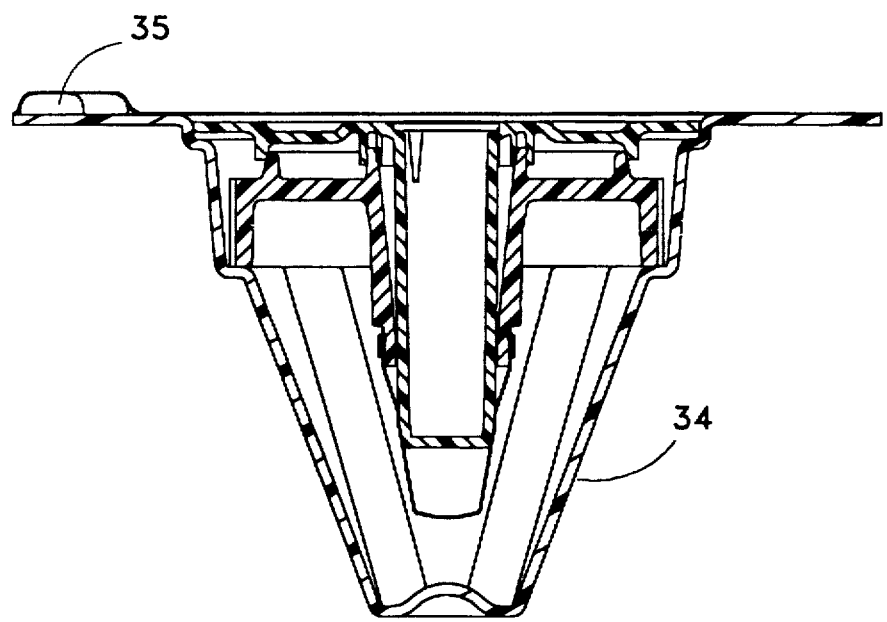
FIG. 5 is a side view of the dialysis apparatus of FIG. 4 held within a disposable container.

The unit may be readily sealed in a disposable vacuum formed container shown in FIG. 5 and indicated by reference character 34. Container 34 is provided with a peel-off cover 35 so that the apparatus may be maintained in a sterilized condition and opened just before use.

Figure 6:
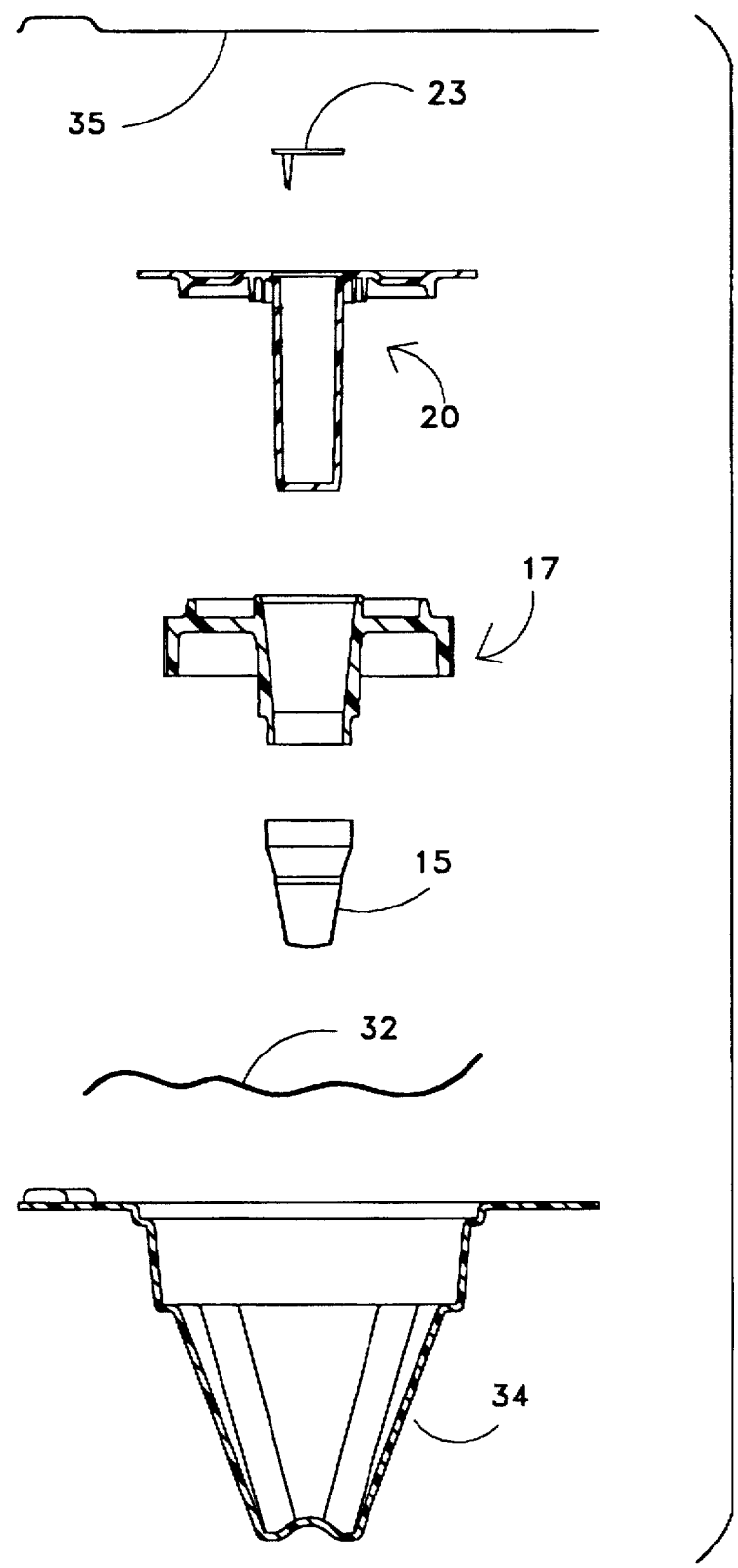
FIG. 6 is an exploded cross-sectional side view of the apparatus of FIG. 5.

The unit of FIG. 5 is shown in exploded side view in FIG. 6 and it is preferable that a series of containers 34 having square tops be supplied in a sheet of. for instance. 12 units on one sheet, for ease in packaging and shipping.

The membrane support ring 17 is shown in side view in FIG. 7 and in top view in FIG. 8. Similarly. the insert cup 21 is shown in side view in FIG. 9 and top view in FIG. 10. An example of the ability of the device of the present invention to accommodate a large range of sample sizes is indicated in FIG. 11 where membrane 36 is shown in an elongated fluted version combined with the identical membrane support ring 17 and an alternative version of insert member 20.

Another advantage of the design of the present invention is its ability to be modified to cover a wide range of sample sizes. This is indicated by the dish bottom 37 of insert member 20' of FIG. 11. The dish bottom 37 permits the placement of very small samples in an inverted positioned insert member and a membrane support ring. also inverted, may then be placed over it and the membrane is small enough to contact the small sample held in dish bottom 37. The fluted membrane 36 shown in FIG. 11 is shown in cross-sectional view in FIG. 13. Membrane 36 is four inches in length. It can be seen that the side walls have inwardly curved portions 38 and outwardly curved portions 39. This provides a larger surface area than a cylindrical membrane would provide. It also adds structural strength to the dipped membrane and permits sample sizes as large as 5 milliliters with the apparatus of the present invention.

Figures 11, 12, 13:
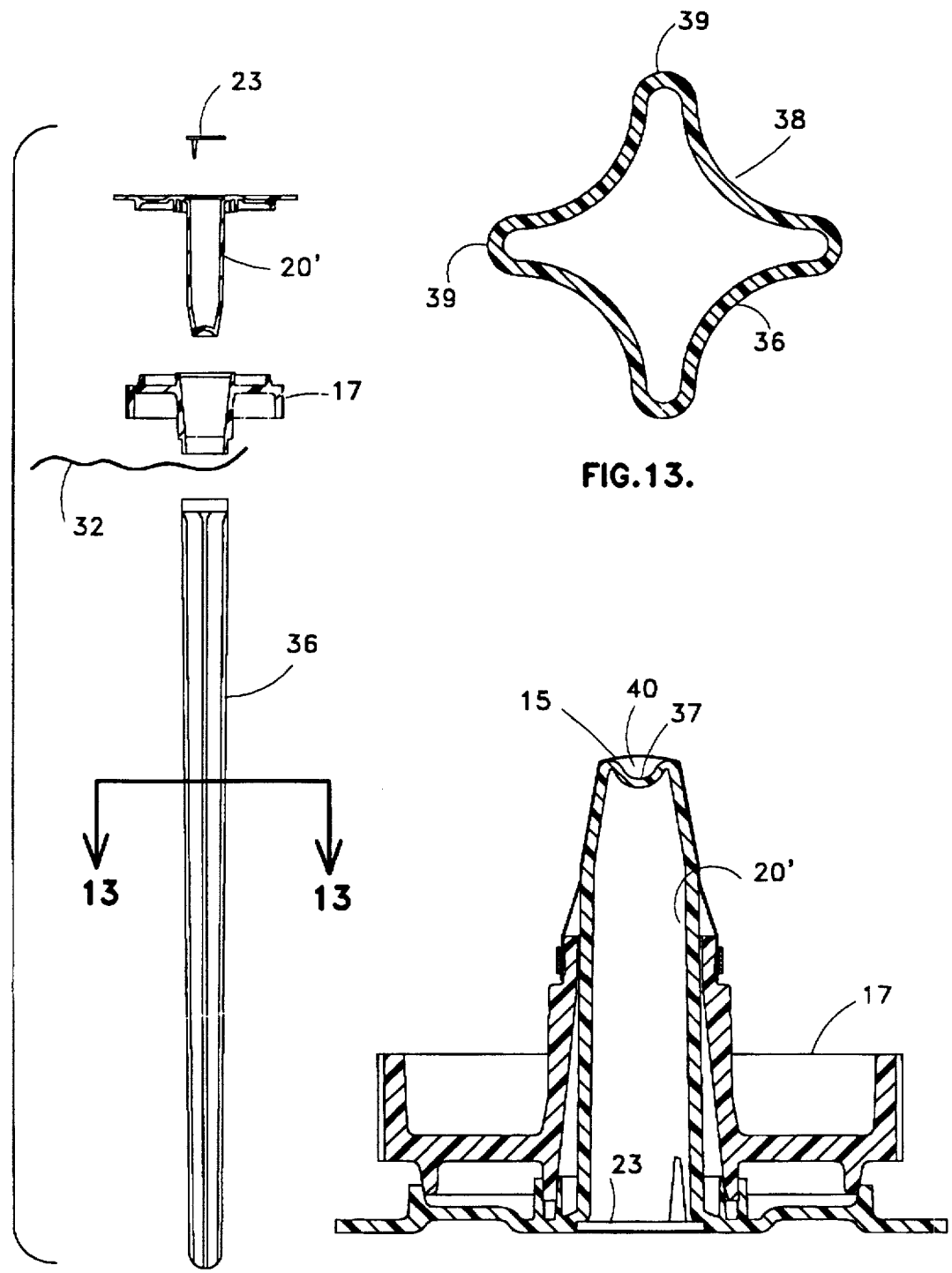
FIG. 11 is a cross-sectional side view of an alternate configuration of the dialysis apparatus of FIG. 1.
FIG. 12 is a cross-sectional view of the dialysis apparatus of FIG. 10 in an inverted configuration.
FIG. 13 is a cross-sectional view taken along line 13—13 of FIG. 11.

On the other end of the scale, the dish bottom 37 holds a sample as small as 10 microliters, as shown in FIG. 12 and indicated by reference character 40., while the membrane 15 is the same as the membrane shown in FIG. 1. Because of the shape of the insert 20', the sample size can be changed without changing the membrane support ring 17 or the membrane 15. This provides the ability to process samples of a very wide range of sample sizes.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

I claim:

1. A disposable dialysis apparatus suspended in a dialysate solution, said disposable dialysis apparatus and dialysate solution comprising:

a dialysate solution;

a membrane support ring having an upper plate with a central opening. a membrane support tube having an open top and an open bottom, said tube extending downwardly to said open bottom from said opening in said upper plate; and a membrane with an open top which is sealed around said open bottom of said membrane support tube, said membrane having a closed side wall and a closed bottom, said membrane support ring including means to cause said membrane support ring and said membrane to float in a dialysate solution so that the membrane is positioned at the bottom of the assembly completely immersed in said dialysate solution.

2. The disposable dialysis apparatus of claim 1 further including an insert having an upper portion extending to an insert cup having side wall and a closed bottom, said insert cup extending into said membrane support tube and said insert cup having an outer edge adjacent the closed bottom and wherein said closed bottom of said insert cup extends into said membrane.

3. The disposable dialysis apparatus of claim 2 wherein said outer edge above the bottom of said insert cup is shaped to seal against an inner surface of said membrane.

4. The disposable dialysis apparatus of claim 3 wherein said outer edge above the bottom of said insert cup is tapered and said inner surface of said membrane is tapered to mate with said outer edge.

5. The disposable dialysis apparatus of claim 2 wherein said central opening of said membrane support ring is tapered so that the top is wider than the bottom to facilitate the insertion of said insert cup into said central opening.

6. The disposable dialysis apparatus of claim 1 wherein said membrane support ring includes a downwardly depending air seal to capture air between said downwardly depending air seal, said upper plate of said membrane support ring and said membrane support tube when said assembly is placed on the surface of the dialysis solution.

7. The disposable dialysis apparatus of claim 2 wherein said membrane support ring has a pair of upwardly extending dams which form an air tight seal with a pair of spaced downwardly depending dams on a lower surface of said upper portion of said insert so that a volume of air is captured between said dams so that the assembly will float in said dialysate solution.

8. The disposable dialysis apparatus of claim 2 wherein said insert cup has a cap on the top of the insert cup.

9. The disposable dialysis apparatus of claim 8 wherein said cap includes membrane type indicating indicia.

10. The disposable dialysis apparatus of claim 2 wherein said upper portion of said insert extends outwardly with respect to said membrane support ring to facilitate removal of said insert from said membrane support ring.

11. The disposable dialysis apparatus of claim 1 wherein said membrane is affixed to the open bottom of said membrane support tube by a suture placed about a portion of said membrane adjacent its open top against an outer tie cone formed on the outer surface of said membrane support tube adjacent its open bottom.

12. A disposable dialysis apparatus comprising:

a membrane support ring having a membrane support tube having an open top and an open bottom;

an insert member having an insert cup within said membrane support tube, said insert cup having a closed bottom, said closed bottom extending below said open bottom of said membrane support tube, said insert member having an upper portion which extends above said membrane support ring; and a cup-shaped membrane affixed about the open bottom of said membrane support tube, said cup shaped membrane being formed so that it has a closed bottom.

13. The disposable dialysis apparatus of claim 12 wherein said closed bottom of said insert cup forms a seal against the inner surface of said cup-shaped membrane.

14. The disposable dialysis apparatus of claim 13 wherein said insert cup has an outer surface extending upwardly from its closed bottom and said outer surface is tapered and said inner surface of said membrane has a matching taper.

15. The disposable dialysis apparatus of claim 12 wherein said membrane is affixed to said membrane support tube with a suture.

16. The disposable dialysis apparatus of claim 12 wherein the closed bottom of said insert cup is dished inwardly to form a sample re ceiving dish.

17. The disposable dialysis apparatus of claim 12 wherein said insert cup has a closed side wall and a closed top to form a closed chamber between the closed top, the closed side walls and the closed bottom.

* * * * *